United States Patent
McDonnell et al.

(10) Patent No.: US 7,001,873 B2
(45) Date of Patent: Feb. 21, 2006

(54) DECONTAMINATION OF SURFACES CONTAMINATED WITH PRION-INFECTED MATERIAL WITH OXIDIZING AGENT-BASED FORMULATIONS

(75) Inventors: Gerald E. McDonnell, Chardon, OH (US); Herbert J. Kaiser, Pontoon Beach, IL (US); Kathleen M. Antloga, Chardon, OH (US); Jennifer A. Scocos, North Royalton, OH (US)

(73) Assignee: Steris Inc., Temecula, CA (US)

( * ) Notice: Subject to any disclaimer, the term of this patent is extended or adjusted under 35 U.S.C. 154(b) by 342 days.

(21) Appl. No.: 10/098,767

(22) Filed: Mar. 14, 2002

(65) Prior Publication Data
US 2003/0073592 A1    Apr. 17, 2003

Related U.S. Application Data

(60) Provisional application No. 60/327,460, filed on Oct. 5, 2001.

(51) Int. Cl.
*C11D 1/00* (2006.01)
*C02F 5/08* (2006.01)

(52) U.S. Cl. .................... 510/161; 510/218; 422/13; 422/28

(58) Field of Classification Search ................ 510/375, 510/379, 380, 382, 384, 386, 387, 388, 161, 510/218; 422/13, 28
See application file for complete search history.

(56) References Cited

U.S. PATENT DOCUMENTS 5,116,575 A * 5/1992 Badertscher et al. .......... 422/28
5,567,444 A * 10/1996 Hei et al. .................... 424/616

FOREIGN PATENT DOCUMENTS

| FR | 2759589 | 8/1998 |
|---|---|---|
| WO | WO 98/15297 | 4/1998 |
| WO | WO 01/54736 A2 | 8/2001 |

OTHER PUBLICATIONS

MSDS data sheet for the STERIS 20®Sterilant Concentrate.*
Antloga, et al. "Prion Disease and Medical Devices", ASAIO Journal, V. 46, N. 6, 2000; pp. S69-S72 XP001092854.
Darbord, "Inactivation of Prions in Daily Medical Practice", Biomedicine & Pharmacotherapy, V. 54, 1999 pp. 34-38 XP002228686.
Rutala, et al., "Creutzfeld-Jakob Disease : Recommendations for Disinfection and Sterilization", Clinical Infectious Diseases, V. 32, N. 9, May 2001 pp. 1348-1356 XP008012867.
Samson, "Stérilisation du Matériel de Dermato-Chirurgie au Cabinet du Dermatologue", Nouvelle Dermatologiques, V. 19, N. 1, 2000 pp 57-60 XP008012868.
Antloga, K., J. Meszaros, P.M. Malchesky, and G.E. McDonnell (2000). Prion Disease and Medical Devices, ASAIO J 46: S69-S72.
Baron, H., J. Safar, D. Groth, S.J. DeArmond, and S.B. Prusiner (2001). Prions, *In*, Disinfection, Sterilizaton and Preservation (Ed. S.S. Block), 5th edition, pp. 659-674, Lippincott, Williams & Williams, New York.
Yon, J.M. (2001), Protein Folding: A Perspective for Biology, Medicine and Biotechnology, Brazil. J. Med. Biol. Res. 34:419-435.

* cited by examiner

*Primary Examiner*—Yogendra N. Gupta
*Assistant Examiner*—John M. Petruncio
(74) *Attorney, Agent, or Firm*—Fay, Sharpe, Fagan, Minnich & McKee, LLP (57) ABSTRACT

A surface which carries a material which is infected with prions is cleaned with an alkaline cleaning solution to remove as much proteinaceous material as possible from the surface. The cleaning agent is an alkaline cleaning agent which attacks prions remaining on the surface and which attacks prions removed from the surface during the cleaning step. After the cleaning solution is drained, a solution of surfactants, buffers, and heavy metal free corrosion inhibitors is circulated over the surface at 50°–60° C. The surfactants disperse and unclump the prion-contaminated material. A strong oxidant, preferably peracetic acid, is added to the solution to bring the peracetic acid concentration to 1,000–2,500 ppm. The peracetic acid or other strong oxidant attacks the prions, particularly the unclumped prion strands, deactivating the prions. After rinsing and drying, the surface may be wrapped in a microbe impermeable barrier and subjected to terminal sterilization, such as steam autoclaving.

25 Claims, 6 Drawing Sheets

DECONTAMINATION OF SURFACES CONTAMINATED WITH PRION-INFECTED MATERIAL WITH OXIDIZING AGENT-BASED FORMULATIONS

This application claims the priority of U.S. Provisional Application Ser. No. 60/327,460, filed Oct. 5, 2001.

BACKGROUND OF THE INVENTION

The present application relates to prion deactivation. It finds particular application in conjunction with the deactivation of prion infected materials from medical and surgical instruments and will be described with particular reference thereto. However, it is to be appreciated that the present invention will also find application in conjunction with the decontamination of other surfaces contaminated with prion infected material such as pharmaceutical preparation facilities, food processing facilities, laboratory animal research facilities including floors, work surfaces, equipment, cages, fermentation tanks, fluid lines, and the like.

Prions are proteinaceous infectious agents which cause similar fatal brain diseases, known as transmissible spongiform encephalopathies (TSEs). These diseases include Creutzfeldt-Jakob disease (CJD) in humans, Bovine Spongiform Encephalopathy (BSE) in cattle, also known as "mad cow" disease in humans, Scrapie in sheep, and Wasting disease in elk and deer. These diseases are characterized by initially long incubation times. Once neurological signs, such as dementia or loss or coordination, become apparent, relatively rapid neurological degradation follows leading to death. The prions are believed to be an abnormal form of a protein commonly found in the host. However, unlike the normal form of the protein, the host is unable to break down the abnormal form. The abnormal proteins accumulate, particularly in neural tissue, eventually causing neural cell death.

Although not considered to be highly contagious, prion diseases can be transmitted by certain high risk tissues, including the brain, spinal cord, cerebral spinal fluids, and the eye. After a surgical procedure on a prion infected patient, prion containing residue may remain on the surgical instruments, particularly neurosurgical and opthalmological instruments. During the long incubation period, it is extremely difficult to determine whether a surgical candidate is a prion carrier.

Prions are very resistant to deactivation. Unlike microorganisms, prions have no DNA or RNA to destroy or disrupt. Prions, due to their hydrophobic nature, tend to aggregate together in insoluble clumps. Under many conditions that lead to successful sterilization in microorganisms, prions form tighter clumps which protect themselves and underlying prions from the sterilization process. The World Health Organization (1997) protocol for prion deactivation calls for soaking the instrument in concentrated sodium hydroxide or hypochlorite for two hours followed by one hour in an autoclave. This process is, of course, damaging to many medical instruments and destructive of others.

The present application provides a new and improved prion deactivation technique which overcomes the above-referenced problems and others.

SUMMARY OF THE INVENTION

In accordance with the present invention, surfaces contaminated with potentially prion-infected materials are cleaned using an alkaline cleaner which cleans and attacks any prions remaining on the instruments. After cleaning, the instrument is treated with an oxidizing agent in liquid or gaseous form.

In accordance with a more limited aspect of the present invention, the oxidizing agent is in liquid form in solution with surfactants which open up the prion molecules and allow the oxidizing agent to break down the proteins more effectively.

In accordance with a yet more limited aspect of the present invention, the liquid oxidizing agent solution is maintained at about 53–57° C.

In accordance with a yet more limited aspect of the present invention, the oxidizing agent is buffered to a near neutral pH.

In accordance with a yet more limited aspect of the present invention, the oxidizing agent includes peracetic acid.

In accordance with another more limited aspect of the present invention, the instrument is treated with the liquid oxidizing agent for less than 12 minutes.

One advantage of the present invention is that it is gentle on instruments.

Another advantage of the present invention is that it deactivates prions quickly and effectively.

Another advantage of the present invention is that it is compatible with a wide variety of materials and devices.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Instruments or other items which carry material which may be contaminated with prions are subject to a cleaning operation using an alkaline cleaner. The cleaner is preferably formed by dilution of a concentrate which includes an alkaline cleaning agent, and optionally includes one or more of the following: a surfactant, a cationic polymer, a chelating agent, an anti-redeposition agent, a cationic polymer, and a corrosion inhibitor.

The alkaline cleaning agent is preferably a hydroxide of an alkali or an earth alkali metal. Exemplary cleaning agents are potassium hydroxide and sodium hydroxide. The hydroxide is preferably present at from 20–60% by weight of the concentrate.

The chelating agent is provided for chelating with water hardness salts, such as salts of calcium and magnesium, deposited on the equipment to be cleaned. Suitable chelating agents include, but are not limited to, carboxylic acid-based polymers, such as polyacrylic acid, and ethylenediaminetetraacetic acid (EDTA) or salts thereof. Sodium hexametaphosphate, discussed below, also acts as a chelating agent to some extent. The chelating agent is preferably present from about 1–15% by weight of the concentrate. A preferred composition includes 2–10% by weight of Na-EDTA, and 0.1–3% by weight of polyacrylic acid.

The surfactant is selected from the group consisting of anionic, cationic, nonionic and zwitterionic surfactants to enhance cleaning performance. Examples of such surfactants include but are not limited to water-soluble salts or higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

Additional examples are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Suitable amphoteric surfactants are alkyl amphocarboxylates, such as mixed C-8 amphocarboxylate surfactants. A preferred concentrate includes mixed C8 amphocarboxylates at a concentration of 0–5% by weight.

The anti-redeposition agent inhibits redeposition of soil on the equipment. Suitable anti-redeposition agents include gluconates, such as sodium gluconate, and citrate salts. Polyacrylic acid also acts as an anti-redeposition agent. The anti-redeposition agent is preferably at a concentration of 1–10% by weight of the concentrate composition. A particularly preferred composition includes polyacrylic acid at a concentration of 0.1–3%, more preferably about 0.3% by weight, and sodium gluconate at a concentration of 1–10%, more preferably about 1–5% by weight of the composition.

The cationic polymers aid in maintaining magnesium, silicate and zinc compounds in solution, maintain corrosion inhibitors in solution, and aid in preventing water-hardness precipitation and scaling on the cleaning equipment surfaces when the cleaning compositions of this invention are used in hard water. Exemplary of such cationic polymers are carboxylated polymers which may be generically categorized as water-soluble carboxylic acid polymers, such as polyacrylic or polymethacrylic acids or vinyl addition polymers. Of the vinyl addition polymers contemplated, maleic anhydride copolymers as with vinyl acetate, styrene, ethylene, isobutylene, acrylic acid and vinyl ethers are examples.

Exemplary cationic polymers are dialkyldiallyl ammonium salt (e.g., halide) homopolymers or copolymers, such dimethyidiallyl ammonium chloride homopolymer, dimethyldiallyl ammonium chloride/acrylamide copolymer, dimethyidiallyl ammonium chloride/acrylic acid copolymer, and vinyl imidazolelvinyl pyrrolidone copolymers. Other suitable non-cellulosic cationic polymers are disclosed in the CTFA Cosmetic Ingredient Dictionary under the designation "Polyquaternium" followed by a whole number. All of the above-described polymers are water-soluble or at least colloidally dispersible in water. Such low molecular weight carboxylated polymers, molecular weight range from about 1,000 to less than 100,000, act as antinucleating agents to prevent carbonate from forming undesirable scaling in wash tanks. Polyquaternium 7, a dimethyldiallyl ammonium chloride/acrylamide copolymer, is exemplary. The cationic polymer is preferably present at 0–10% by weight of the concentrate.

Exemplary metal corrosion inhibitors are silicic acid salts and phosphoric acid salts in an amount of about 0–10% weight % of the concentrate.

The cleaning concentrate optionally includes a low level of an antimicrobial agent, such as a phenol, quaternary ammonium compound, or oxidizing agent, e.g., sodium hypochlorite, hydrogen peroxide, or peracetic acid.

A preferred alkali cleaner concentrate is shown in TABLE 1.

TABLE 1

| Ingredient | Recommended Range, wt. % in concentrate |
|---|---|
| 45% Potassium hydroxide | 45–90 |
| 40% Ethylenediamine tetraacetic acid (EDTA), tetrasodium salt | 1–20 |
| Sodium gluconate | 0–7 |
| 30% 2-Propenoic acid homopolymer (Polyacrylic acid) | 1–20 |
| Mixed C8 amphocarboxylates | 0–5 |
| Sodium hexametaphosphate | 0–10 |
| 40% silicic acid, sodium salt | 0–10 |
| 48% acrylic acid homopolymer | 1–20 |
| Dimethyldiallyl ammonium chloride and acrylamide copolymer (Polyquaternium 7) | 0–10 |

In particular, the following formulations are specified in TABLE 2.

TABLE 2

| Component | Formulation A % in Cleaner concentrate | Formulation B % in Cleaner concentrate |
|---|---|---|
| 45% Potassium hydroxide | 69 | 46 |
| 40% Ethylene diamine tetraacetic acid, tetrasodium salt | 20 | 10 |
| Sodium gluconate | 1 | 5 |
| 30% 2-Propenoic acid homopolymer (Polyacrylic acid) | 3 | 1 |
| Mixed C8 amphocarboxylates | 0 | 2 |
| Sodium hexametaphosphate | 0 | 10 |
| Softened water | 7 | 26 |

To perform the cleaning operation, the products are diluted in water at 8–16 cc/liter at 30 to 65° C. for 2 to 30 minutes. An typical overall cycle in an automatic washer may include a two minute pre-wash with water at 30–65° C., 2–30 wash with the alkaline cleaner at 8–16 cc/liter, 15 second rinse in water, one minute thermal rinse at 30–65° C.

and finally a drying step (if required). A further cycle may simply involve prerinsing, alkaline cleaning, and post-rinsing as described above.

The cleaning concentrate optionally includes a low level of an antimicrobial agent, such as phenols, quaternary ammonium compounds, or oxidizing agents, e.g., sodium hypochlorite, hydrogen peroxide, or peracetic acid.

Other cleaners are also contemplated. Cleaners fall into various categories. Enzymatic cleaners include active proteases, lipases, and other enzymes to aid in tissue or soil breakdown on a surface. These products assist in removing prion and other proteinaceous materials, but generally lack efficacy against prions, i.e., prions are protease resistant. Non-enzymatic cleaners may be broken down into neutral, acidic, and alkali based products. These cleaners include a variety of excipients that aid in soil removal from a surface such as wetting agents and surfactants.

Figure 1:
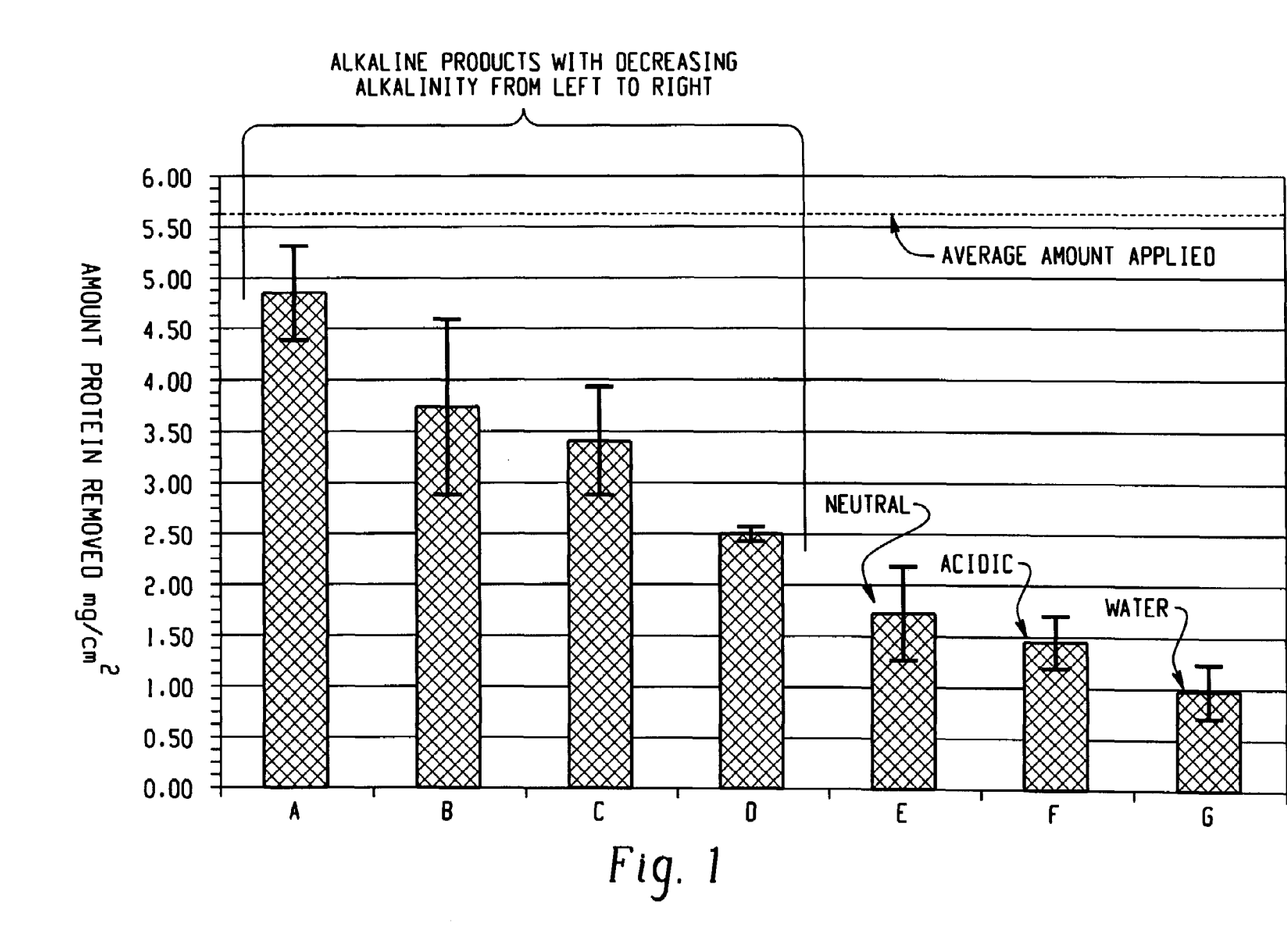
FIG. 1 illustrates proteinaceous material removal with various cleaning compositions.
Figure 2:
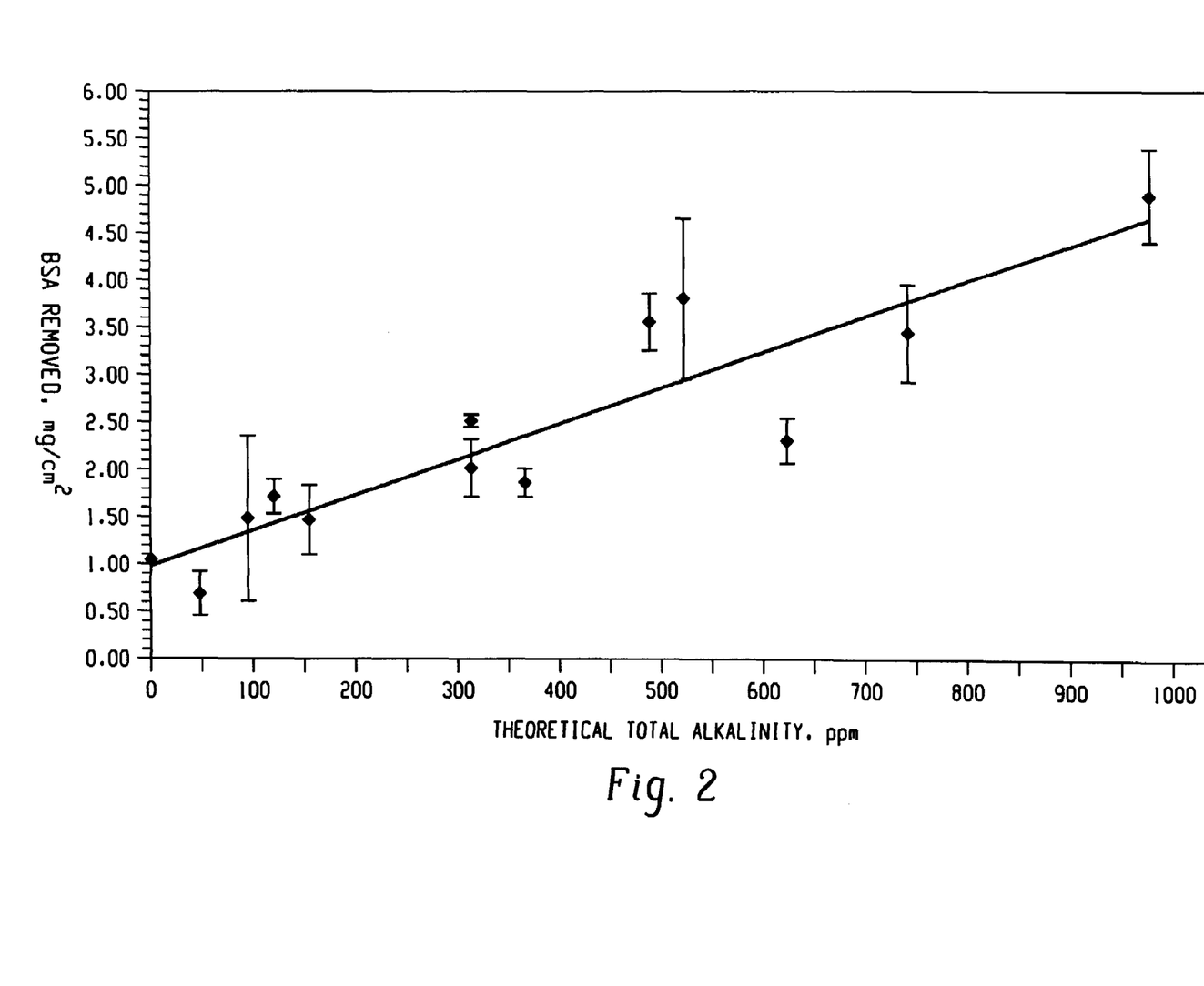
FIG. 2 graphs proteinaceous material versus alkalinity.

Cleaning agents with a range of pHs were tested against a prion model for prion removal efficacy. More specifically, a 5% bovine serum albumin (BSA) solution was prepared and 2 ml pipetted onto each of like stainless steel coupons. These coupons were dried at 43° C. in an oven for one hour, cooled to room temperature, and weighed. Under these drying conditions, bovine serum albumin adopts a high β-sheet confirmation which is similar to infectious prion protein. The coupons were washed in a STERIS 444™ washer/disinfector using its instrument cycle, but with different cleaning compositions. The instrument cycle includes a 2 minute prewash, a 2 minute wash at 65° C., a rinse, a thermal rinse, and a drying cycle. Following the cycle, the coupons were removed from the washer, cooled, and weighed. FIG. 1 shows the amount of material removed in the washing cycle where compositions A, B, C, and D are alkaline cleaners with decreasing alkalinity from A–D, composition E is a neutral cleaner (Renu-Klenz™, available from STERIS Corp., Mentor, Ohio), composition F is an acid cleaner (CIP220™, available from STERIS Corp.), and composition G is a plain water control. FIG. 2 is a graph of the material removed versus total alkalinity in parts per million. As shown in FIG. 2, there is a strong correlation between the amount of material removed and the alkalinity, the amount increasing with the total alkalinity of the cleaning composition.

The cleaning composition used as described removes fixed proteinaceous matter including clumps of protein. Any remaining proteinaceous substances are in the form of a thin film which is more easily penetrated by the deactivating agent in a subsequent deactivation step. Moreover, the preferred alkaline cleaner results in about a 50% destruction of prions in the residual film that is not removed during the cleaning step.

Optimized alkaline cleaning formulations based on Table 1 were developed and analyzed as described above with the following results:

TABLE 3

| Formulation | Average Protein Removed (mg/cm$^2$) | Standard Deviation | Equivalent [KOH], M, in washer |
|---|---|---|---|
| Water Control | 0.5 | 0.04 | 0 |
| Alkaline 1 | 2.36 | 0.57 | 0.020 |
| Alkaline 2 (A) | 4.18 | 0.52 | 0.033 |
| Alkaline 3 | 2.97 | 0.75 | 0.031 |
| Alkaline 4 | 2.52 | 0.29 | 0.029 |
| Alkaline 5 | 3.56 | 0.18 | 0.035 |
| Alkaline 6 | 2.44 | 0.49 | 0.020 |

TABLE 3-continued

| Formulation | Average Protein Removed (mg/cm$^2$) | Standard Deviation | Equivalent [KOH], M, in washer |
|---|---|---|---|
| Alkaline 7 | 2.32 | 0.30 | 0.020 |
| Alkaline 8 | 3.11 | 0.17 | 0.033 |
| Alkaline 9 | 2.85 | 0.74 | 0.034 |
| Alkaline 10 | 3.46 | 0.55 | 0.034 |
| Alkaline 11 | 3.53 | 0.52 | Not determined |
| Alkaline 12 (B) | 4.06 | 0.40 | Not determined |
| Alkaline 13 | 3.34 | 0.42 | Not determined |
| Alkaline 14 | 3.49 | 0.20 | Not determined |
| Alkaline 15 | 3.28 | 0.75 | Not determined |

The compositions of the most effective formulations (labeled A and B) are specified above in TABLE 2.

Figure 3:
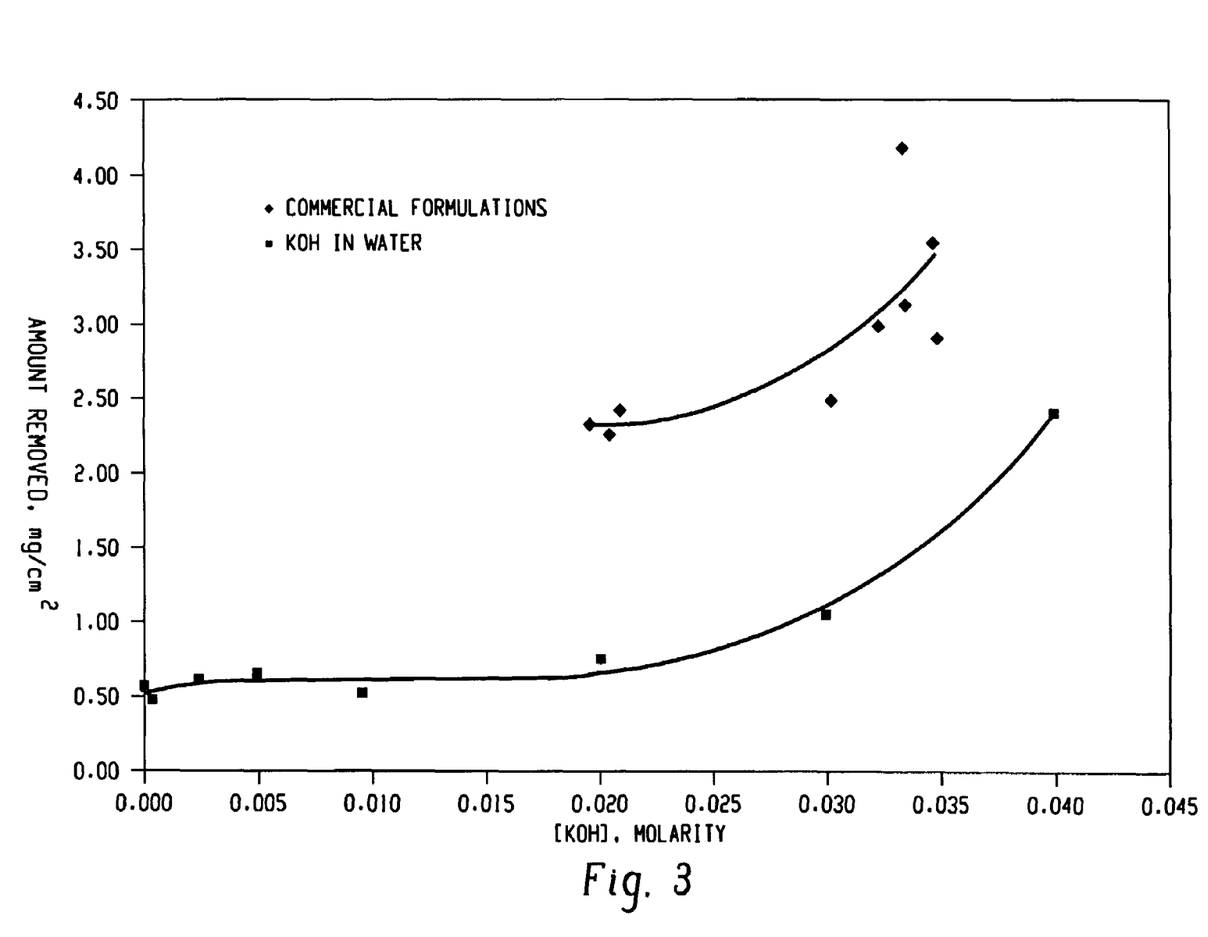
FIG. 3 compares the effect of KOH concentration alone (top curve) and overall alkalinity (bottom curve) in the cleaning formulations in proteinaceous material removal.

The protein removal efficacy is not only a function of alkalinity in these optimized formulations, but on the other components of the composition. This is shown in FIG. 3. The formulations are primarily composed of three component parts: alkalinity ingredients, water control ingredients, and surfactants. The alkalinity ingredients also may act as water control agents. For example, EDTA contributes both alkalinity and water control characteristics to the formulations. Water control agents are preferably included because the quality of the water used to clean surfaces varies considerably and can otherwise affect the efficacy of a given formulation. An example is water hardness, which displays inverse solubility, the higher the temperature the less soluble the water hardness salts are. Water hardness salts are also less soluble at higher pH values. Therefore, the EDTA or other chelating agents are preferably employed to keep the hardness salts in solution. All three of the above component parts are believed to function synergistically to enable the formulation to clean surfaces. This is demonstrated in FIG. 3 which compares the alkalinity equivalents of nine formulations to that of KOH alone as the alkalinity source.

The effect of alkalinity alone was evaluated by adding the respective proportion of potassium hydroxide (KOH) to the washer and testing as described above. Although the effect of alkalinity (expressed as the molarity of KOH) was significant (as demonstrated in the bottom curve), the formulations tested (examples 1 to 9 from TABLE 3) demonstrated enhanced efficiency of protein removal.

The present inventors have found that proper selection of the cleaning composition not only removes prions and other proteinaceous materials, but also at least partially deactivates the prions. Particularly, alkaline cleaners are significantly more effective in deactivating prions than enzymatic, neutral, or acid cleaners.

Figure 4:
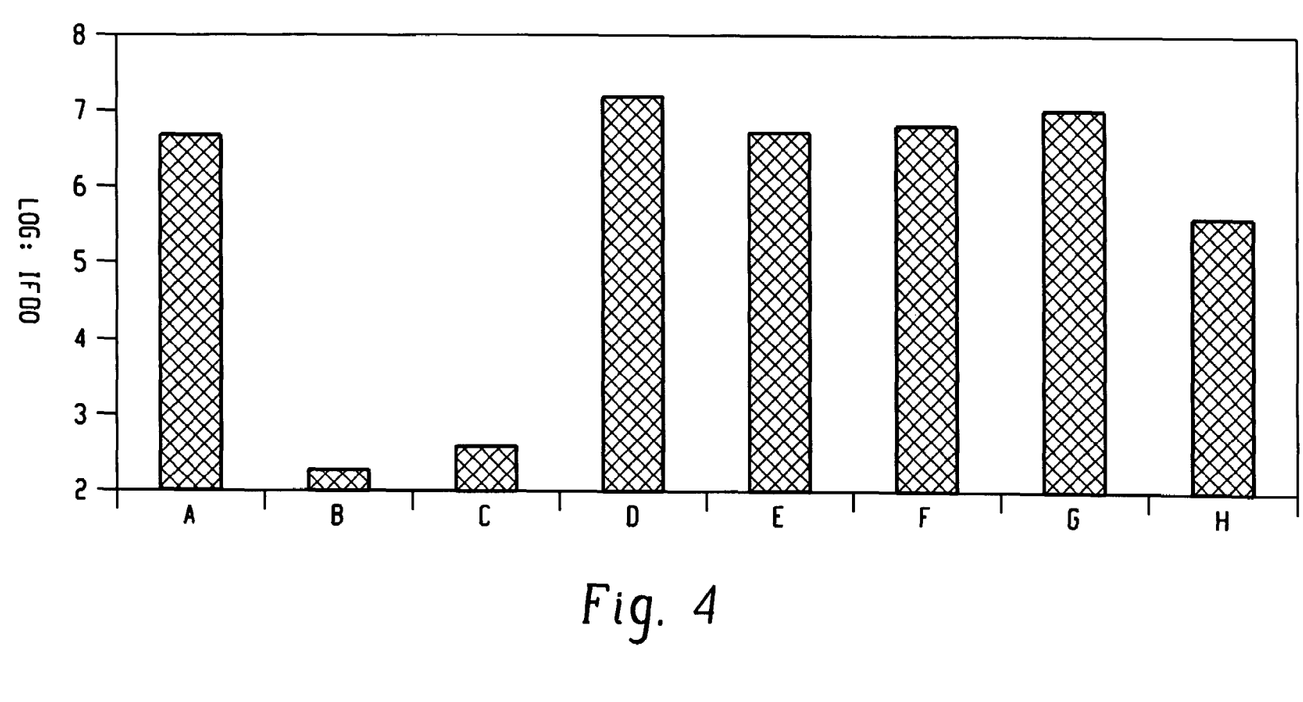
FIG. 4 compares the efficacy of various cleaning compositions in the reduction of a prion (IFDO) model.

A variety of cleaners were tested against a prion model in which ileal fluid dependent organisms (IFDOs) were artificially cultured in modified Mycoplasma based broth, quantified by serial dilutions, and plated on a similar agar. The formulations were prepared in water and an aliquot of IFDO suspended directly into each. The test solutions were incubated at 40° C. for 30 minutes, aliquot sampled and quantified by serial dilution and plating into modified Mycoplasma agar. Following incubation at 37° C. for 48 hours, the plates were counted and log reductions in the IFDO present obtained. These test results are illustrated in FIG. 4, where cleaner A is a control of plain water, cleaner B is an alkaline cleaner (CIP150™), cleaner C is a second, slightly less alkaline cleaner (CIP100™), cleaners D (Klenzyme™) and E (Enzycare 2™) are enzyme cleaners, cleaners F (Renu-Klenz™) and G (NpH-Klenz™) are neutral cleaners, and cleaner H (CIP 220™) is an acid cleaner. (Each of the tested cleaners was obtained from STERIS Corp.)

Thus, alkali cleaners are not only more effective in removing prion material, they are also significantly more effective in deactivating what prion material might remain, as well as removed prion material still in solution.

After the cleaning step, the instruments or other items are subject to a prion deactivation step. During the prion deactivation step, the items are contacted with a liquid or gaseous oxidizing agent. Preferably, the items are immersed in a liquid oxidizing agent which is circulated over all surfaces and through any internal passages or cavities. Alternately, the liquid oxidizing agent is sprayed on all surfaces of the item to be prion deactivated. As yet another alternative, the oxidizing agent is delivered in gaseous or vapor form. In a preferred embodiment, the oxidizing agent includes a peracid, such as peracetic acid. However, other strong oxidants such as hypochlorite or hydrogen peroxide are also contemplated.

In a preferred embodiment, a water-based solution of anti-corrosive agents which are free of heavy metals which tend to degrade peracetic acid and other oxidants, chelating or sequestering agents, surfactants which are effective to unravel the twisted prion strands, and a pH buffer are circulated over all surfaces of the items. Peracetic acid is then added to the solution, either in liquid form or in the form of reagents which react to form peracetic acid. The peracetic acid is added in sufficient quantity to bring its concentration in the solution up to 1,000–3,000 ppm, more preferably 2,000–2,500 ppm.

Looking more specifically to the preferred formulation, the corrosion inhibitors are free of heavy metals such as molybdenum, chromium, cobalt, vanadium, and iron, which are excellent corrosion inhibitors but tend to degrade peracetic acid. Preferred corrosion inhibitors include sulfates and borates for protecting aluminum and steel, including stainless steel, against corrosion. 8-hydroxyquinoline and ortho-phenylphenol are also preferred aluminum corrosion inhibitors. Organic corrosion inhibitors, such as azoles, benzoates, tolytriazoles, and mercaptobenzothiazole are preferred copper and brass corrosion inhibitors. Zeolites and phosphates, which are discussed in greater detail below in conjunction with the buffering system, also inhibit corrosion, particularly in ferrous metals.

A buffering system buffers the pH of the solution to a near neutral pH, preferably a pH of 6.5–8, more preferably 6.5–6.6.

In the preferred embodiment, the buffering system includes phosphates, particularly monosodium phosphate, disodium phosphate, sodium hexametaphosphate, and potassium equivalents thereof. Most preferably, the buffering system includes a mixture of two or more phosphates, such as monosodium phosphate, which is relatively acidic, and disodium phosphate which has a higher pH. The ratio is determined to achieve the selected pH.

In another embodiment, the buffering system includes one or more sodium silicates or zeolites in place of one or all of the phosphates. The zeolites are again used to buffer the solution to the selected pH. Zeolites have the further advantage of providing corrosion inhibition to alkali attacks on surfaces. Zeolites have the general formula $Na_2O.(SiO_2)_x$, where x is the ratio of silica to alkali and is the range of 0.4:1 to 4.0:1, preferably in the range of 1.60:1 to 3.25:1. Suitable zeolites include zeolites sold under the trade names AD40NX and METSO, available from PQ Corporation of Valley Forge, Pa. Preferred compositions include 10–90% by weight zeolites, more preferably around 20–50%.

When the dilutant water is relatively hard, it contains calcium and magnesium salts which tend to precipitate and leave deposits on the instruments and parts of the system. In order to inhibit such precipitation, one or more chelators or sequestering agents (referred to herein generally as chelating agents) is included to complex the metals in these salts. Suitable chelating agents include ethylene diaminetetraacetic acid (EDTA) and salts thereof, nitrilotriacetic acid, and salts thereof, sodium polyacrylates, and combinations thereof. Chelating agents, such as sodium hexametaphosphate are also preferred. Of course, if the solution is formed with deionized water, the chelating agents may be eliminated. To accommodate various city water systems, the composition preferably contains a total of about 1–30% by weight of chelating agents, more preferably 10–15%.

The surface tension reducing agent, i.e., a wetting agent or surfactant, is added to the composition to increase penetration into crevices and to untwist and open out the prion filaments. Various surface energy reducing agents are contemplated including anionic, cationic, nonionic, amphoteric, and/or zwitterionic surfactants. Preferred nonionic wetting agents include surfactants such as fatty alcohol polyglycol esters, nonylphenoxypoly (ethyleneoxy) ethanol, and ethoxylated polyoxypropylene, and other nonionic surfactants. Specific examples include Genapol, UD-50™, IGEPAL™, FLUOWET™, ANTAROX™, and PEGOL™.

The surfactant is preferably present in an amount from 0.01% to about 8% by weight.

10–20 grams per liter of the corrosion inhibitor, buffer, chelating agent, and surfactant mixture described above are mixed with water (preferably deionized or softened water) to form a preconditioning solution which is heated to 45°–60° C., more preferably 53–57° C., and circulated over the instruments for 1–2 minutes to precondition the proteinaceous substances on the surface. Thereafter, liquid peracetic acid or reagents which react to form peracetic acid are added to the solution. For example, 5–8 grams per liter of 35% peracetic acid achieve an appropriate 2,000–2,500 ppm. Alternatively, acetylsalicylic acid and perborate can be added to and react in the solution to generate peracetic acid of this concentration.

The peracetic acid solution is circulated over the instruments for 8–20 minutes, preferably 10–12 minutes.

After the treatment with the peracetic acid solution, the peracetic acid solution is drained and the instruments are rinsed, preferably with a sterile or microbe-free rinse water. After rinsing, the instruments are dried.

A preferred treatment method thus includes: treatment of prion contaminated (or suspected prion-contaminated) materials or devices with an alkaline cleaner solution, followed by a water rinse. The materials or devices are then treated with a pretreatment solution comprising one or more of chelating agents, surfactants, a buffering system, and a corrosion inhibitor. The materials or devices are then treated with a liquid oxidizing agent which is readily formed by adding the oxidizing agent, peracetic acid in the preferred embodiment, to the pretreatment solution. One or more rinse steps follow. The cleaner solution, water rinses, pretreatment solution, and liquid oxidizing agent are preferably applied by immersing the contaminated materials or devices in a flow of the respective liquid, by spraying the liquid onto the surfaces of the devices or materials, or a combination of both.

Stainless steel instruments, such as surgical instruments may then be wrapped in a microbe impenetrable wrap and subject to a terminal sterilization process to kill any microorganisms on the surface. Suitable terminal sterilization processes for stainless steel instruments include steam autoclaving and vapor hydrogen peroxide treatment. Instruments which are not amenable to steam sterilization can be wrapped and terminally sterilized using vapor hydrogen peroxide.

Without intending to limit the scope of the invention, the following examples show the effects of compositions and conditions on prion deactivation and/or removal.

EXAMPLE 1

Coupons were prepared by treating them with a prion model (a BSA denatured protein). The coupons were then treated with a composition containing 1,000 mg per liter concentration of peracetic acid at temperatures from 40°–60° C. The composition also contained a surfactant system, a phosphate buffering system, an organic corrosion inhibitor, and a chelating agent. The composition was free of heavy metals.

TABLE 4 summarizes the amounts of BSA broken down during a 12 minute exposure to the composition.

TABLE 4

| Temperature (° C.) | Percent Protein Breakdown at 1000 mg/L Peracetic Acid |
|---|---|
| 0 | 0 |
| 30 | 1 |
| 40 | 1 |
| 45 | 1 |
| 50 | 90 |
| 55 | 99 |
| 60 | 80 |

The results indicate that little, if any, protein breakdown occurred at 40° C. and 45° C. At 50° C. and 55° C., the proteins were effectively broken down. At 60° C., some protein residue remained, suggesting clumping. That is, at temperatures of about 60° C. and above, the protein aggregates and protects itself with higher resistance to attack by peracetic acid or other strong oxidants.

The effect of peracetic acid concentration on the same BSA model was also studied. Coupons treated with the BSA model were treated with various concentrations of peracetic acid at 50° C. for 12 minutes. Results are summarized in TABLE 5:

TABLE 5

| Peracetic acid Concentration | Percent Protein Breakdown at 1000 mg/L Peracetic Acid |
|---|---|
| 0 | 0 |
| 500 | 0 |
| 1000 | 10 |
| 1500 | 50 |
| 2000 | 95 |
| 2500 | 99 |

The results of TABLE 5 indicate that increasing the concentration of peracetic acid increases breakdown of the model and is expected to have a similar correlation with actual prion breakdown. Accordingly, it is suggested that for rapid breakdown of prions, the peracetic acid concentration is maintained at least 2000 ppm.

EXAMPLE 2

Figure 5:
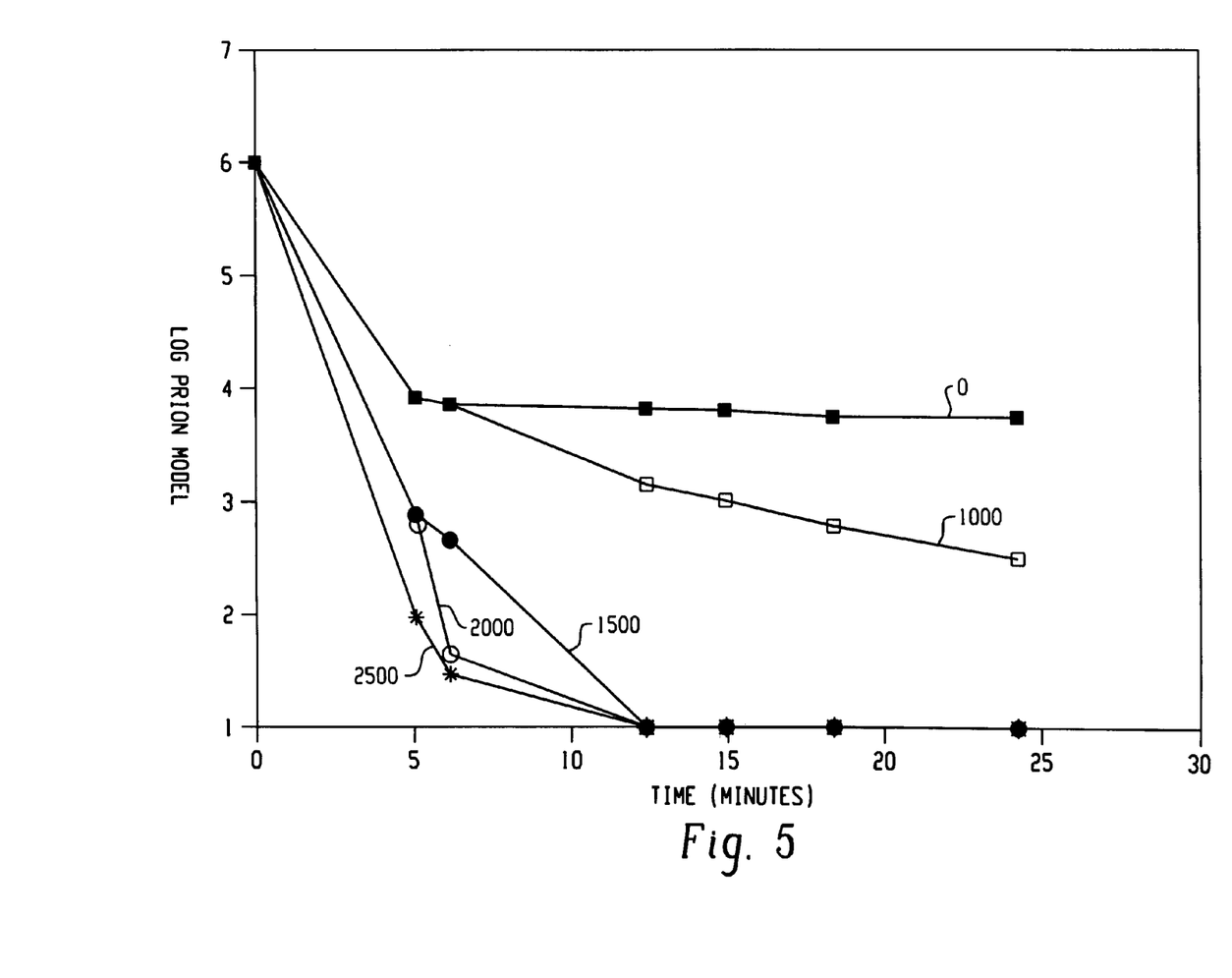
FIG. 5 compares the effect of peracetic acid concentration in the reduction of a prion (IFDO) model.

Coupons of a prion model in the form of ileal fluid dependent organisms (IFDO) were treated with peracetic acid formulations as described in Example 1, having peracetic acid concentrations from 0–2,000 mg per liter, at 50° C., and then cultured in a modified Mycoplasma base broth. An aliquot of the IFDO suspension was added directly to 1,000 mg per liter, 1,500 mg per liter, 2,000 mg per liter, and 2,500 mg per liter peracetic acid solutions at 50° C. The models were then incubated at 37° C. for 48 hours in the modified Mycoplasma broth. FIG. 5 illustrates the log of the prion model versus time for 0; 1,000; 1,500; 2,000; and 2,500 mg per liter solutions. Because higher levels of material on actual instruments can degrade peracetic acid, an initial concentration of 2,500 mg per liter peracetic acid is preferred.

EXAMPLE 3

Figure 6:
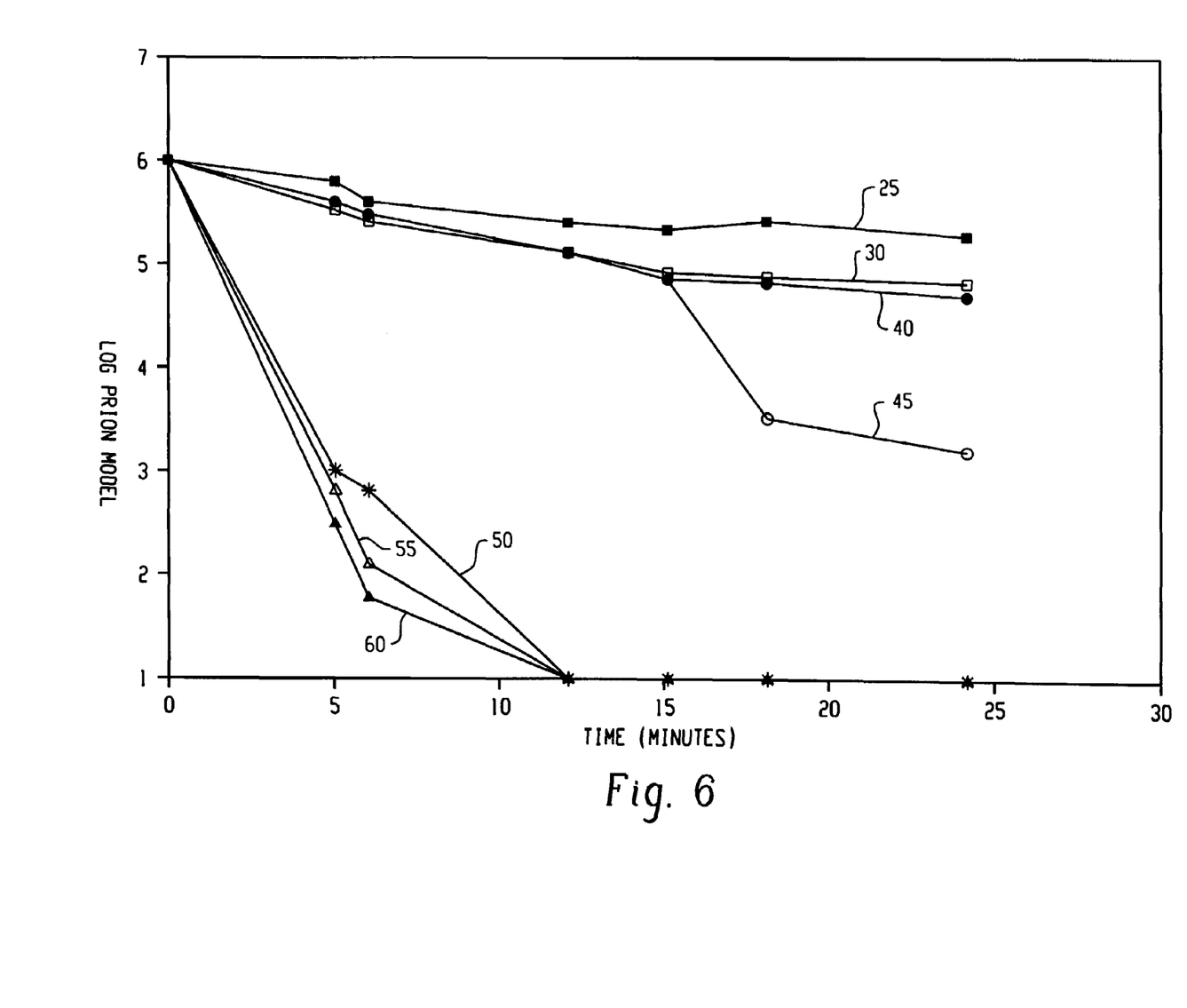
FIG. 6 compares the effect of peracetic acid temperature in the reduction of a prion (IFDO) model.

Coupons of a prion model in the form of ileal fluid dependent organisms (IFDO) were treated with peracetic acid formulations at 1,500 mg per liter at various temperatures, ranging from 25 to 60° C., and then cultured in a modified Mycoplasma base agar as described in Example 2. FIG. 6 illustrates the log reduction of the prion model versus time at 25, 30, 40, 45, 50, 55, and 60° C., respectively. It is considered that the formulation was optimal at temperatures greater than 50° C. However, due to the possibility of protein coagulation at temperatures greater about 60° C. (as demonstrated in TABLE 4), the optimal temperatures for prion denaturation would be 50–60° C., more specifically 53–57° C.

EXAMPLE 4

To test an overall decontamination process, coupons of a prion model in the form of ileal fluid dependent organisms (IFDO) at $10^6$ units per coupon were directly exposed to alkaline cleaners (formulation A and B) prepared in water and gently stirred for 30 minutes. Coupons were removed, directly exposed to a peracetic acid formulation (as described for Example 1) at 2500 mg per liter peracetic acid and 55° C., then cultured in a modified Mycoplasma base agar, as described in Example 2.

The results are summarized in TABLE 6:

TABLE 6

| Treatment | Average IFDO concentration on coupon surface ($Log_{10}$) |
|---|---|
| Untreated control | 6.5 |
| Cleaner Formulation A | 2.9 |
| Cleaner Formulation B | 3.2 |
| Cleaner Formulation A followed by Peracetic acid formulation | <1 |
| Cleaner Formulation B followed by Peracetic acid formulation | <1 |

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of deactivating prions comprising:
   pretreating surfaces that carry prion infected material with an alkaline cleaner having an alkalinity of at least 500 ppm and which unclumps prion strands for a period of from 2 to 30 minutes, the alkaline cleaner being free of oxidizing agents, other than preservatives; and
   treating the surfaces with a peracid in one of liquid and gaseous form to deactivate prions by attacking the unclumped strands.

2. The prion deactivation method as set forth in claim 1 wherein the peracid is a liquid solution which further includes surfactants and a buffer which buffers the pH of the solution to a near neutral pH.

3. The prion deactivation method as set forth in claim 2 wherein the peracid treating step is carried about between 50°–60° C.

4. The prion deactivation method as set forth in claim 3 wherein the peracid includes peracetic acid in a concentration of 2,000–2,500 ppm.

5. The prion deactivation method as set forth in claim 2 further including:
   treating the surface with a water-based solution of surfactants, corrosion inhibitors, and buffers which buffer the solution to a near neutral pH;
   adding a peracid to the solution to create a solution containing the peracid.

6. The prion deactivation method as set forth in claim 5 wherein the corrosion inhibitors are free of heavy metals which act as a catalyst to reduce the peracetic acid concentration.

7. The prion deactivation method as set forth in claim 6 wherein the cleaner and peracid solutions are in a temperature range of 53°–57° C.

8. The prion deactivation method as set forth in claim 1 wherein the peracid includes peracetic acid.

9. The prion deactivation method as set forth in claim 1 wherein the cleaning and treating steps are carried out between 50° C. and 60° C.

10. The prion deactivation method as set forth in claim 2 wherein the peracid solution further includes a corrosion inhibitor.

11. The prion deactivation method as set forth in claim 10 wherein a solution of the surfactants, buffers, and corrosion inhibitors is circulated over the surface for at least one minute, after which the peracid is added to the solution and the solution is circulated over the surface for at least another 6 minutes.

12. The prion deactivation method as set forth in claim 10 wherein the corrosion inhibitors and buffers are free of heavy metals which catalytically degrade peracetic acid.

13. The prion deactivation method as set forth in claim 12 wherein the peracid solution is at least 1,000 ppm peracetic acid.

14. The prion deactivation method as set forth in claim 1 wherein the alkaline cleaner is rinsed from the surfaces prior to the peracid treatment step.

15. The prion deactivation method as set forth in claim 1 wherein the cleaning and peracid treatment steps are carried out in a temperature range between 53° C. and 57° C.

16. A prion deactivation method comprising:
   pretreating surfaces that carry prion infected material with an alkaline cleaner having an alkalinity of at least 500 ppm, the alkaline cleaner being free of oxidizing agents, other than preservatives;
   unclumping prion strands with a surfactant; and
   reacting peracetic acid in one of liquid and gaseous form with the prion infected material, the step of unclumping prion strands preceding the step of reacting with peracetic acid, thereby facilitating reacting the peracetic acid with the prion strands and deactivating the prions.

17. The prion deactivation method as set forth in claim 16 further including:
   buffering the peracetic acid to a near neutral pH and protecting the surface from peracetic acid corrosion with corrosion inhibitors that are free of metals that break down peracetic acid.

18. The prion deactivation method as set forth in claim 16 further including:
   after the peracetic acid treating step, rinsing the surface.

19. The prion deactivation method as set forth in claim 18 further including:
   after rinsing the surface, drying the surface;
   wrapping the surface in a microbe barrier; and
   subjecting the wrapped surface to a terminal sterilization process to kill microbes.

20. A prion deactivation method comprising:
   pretreating surfaces that carry prion infected material with a cleaner diluted in water at 8–16 cc/liter, the cleaner being an alkaline cleaner of the formula:
   20.0–41 wt % potassium hydroxide;
   0.4–8 wt % ethylenediamine tetraacetic acid;
   0.0–7 wt % gluconate salt;
   0.3–6 wt % propenoic acid homopolymer;
   0.0–5 wt % C8 amphocarboxylates;
   0.0–10 wt % sodium hexametaphosphate;
   0.0–4 wt % silicic acid salt;
   0.4–10 wt % acrylic acid homopolymer;
   0.0–10 wt % dimethyldiallyl ammonium chloride and acrylamide copolymer; and
   treating the surfaces with peracid in one of liquid and gaseous form.

21. The prion deactivation method as set forth in claim 20 wherein the alkaline cleaner is of the formula:
   20.0–32 wt % potassium hydroxide;
   4.0–8 wt % ethylenediamine tetraacetic acid;
   1.0–5 wt % sodium gluconate;
   0.3–1 wt % 2-propenoic acid homopolymer;
   0.0–2 wt % mixed C8 amphocarboxylates;
   0.0–10 wt % sodium hexametaphosphate;
   7.0–26 wt % water.

22. The prion deactivation method as set forth in claim 20 wherein the cleaner has an alkalinity of at least 500 ppm.

23. A prion deactivation method comprising:
   pretreating surfaces that carry prion infected material with an alkaline cleaner having an alkalinity of at least 500 ppm, the alkaline cleaner being free of oxidizing agents, other than preservatives; and
   treating the surfaces with a peracid in one of liquid and gaseous form to deactivate prions, the peracid being in a concentration of at least 1000 ppm.

24. The prion deactivation method as set forth in claim 23 further including:
   unclumping prions strands with surfactants to facilitate the peracetic acid reacting with the prion strands and deactivating the prions.

25. A method of deactivating prions comprising:
   washing surfaces that carry prion infected material with an alkaline cleaner to remove prions, the alkaline cleaner free of oxidizing agents, other than preservatives and comprising a surfactant and a hydroxide of an alkali or earth alkali metal, the hydroxide being at a concentration which is obtainable by dilution, at 8–16 cc/liter, a concentrate comprising 45–90 wt % of a 45% hydroxide solution; and after the washing step, treating the surfaces with peracetic acid at a concentration of at least 1000 ppm at a pH of 6.5–8 to deactivate prions.

* * * * *